United States Patent [19]

Aoyama et al.

[11] Patent Number: 4,824,779

[45] Date of Patent: Apr. 25, 1989

[54] METHOD FOR THE DETERMINATION OF THE REDUCED FORM OF NICOTINAMIDE ADENINE DINUCLEOTIDE

[75] Inventors: Norihito Aoyama; Akira Miike; Yoshiaki Shimizu, all of Shizuoka; Toshio Tatano, Numazu, all of Japan

[73] Assignee: Kyowa Medex Co., Ltd., Tokyo, Japan

[21] Appl. No.: 706,404

[22] Filed: Feb. 28, 1985

[30] Foreign Application Priority Data

Feb. 29, 1984 [JP] Japan ................... 59-37623

[51] Int. Cl.⁴ ........................... C12Q 1/26
[52] U.S. Cl. ........................ 435/25; 435/26; 435/28
[58] Field of Search ............. 435/25, 28, 26; 260/386, 388, 389

[56] References Cited

U.S. PATENT DOCUMENTS 4,036,863  7/1977  Karger et al. ................ 260/386
4,448,446  5/1984  Flores et al. ................ 260/391
4,592,996  6/1986  Yamanishi et al. ............ 435/28
4,613,465  9/1986  Yamanishi et al. ............ 260/394

FOREIGN PATENT DOCUMENTS 0029104  5/1981  European Pat. Off. .
0057661  8/1982  European Pat. Off. .
0124909  11/1984  European Pat. Off. .

OTHER PUBLICATIONS

Chem. Abs. vol. 98, No. 17 (1983) 139879k.
Chem. Abs. vol. 90, No. 23 (1979) 182296q.
Pat. Abs. Japan, vol. 9, No. 222 (1945) 60-83598.

Primary Examiner—Robert J. Warden
Assistant Examiner—Stephen C. Wieder
Attorney, Agent, or Firm—Fitzpatrick, Cella, Harper & Scinto

[57] ABSTRACT

The present invention provides a method for the determination of NAD(P)H which comprises reacting a chromogen represented by the following general formula (I):

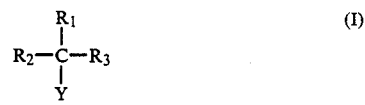

wherein Y is hydrogen or hydroxyl; $R_1$, $R_2$ and $R_3$ may be the same or different, and are groups represented by the following general formula (II), (III) or (IV):

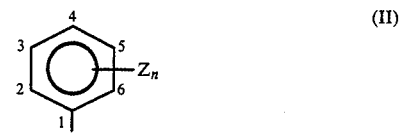

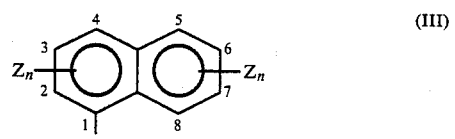

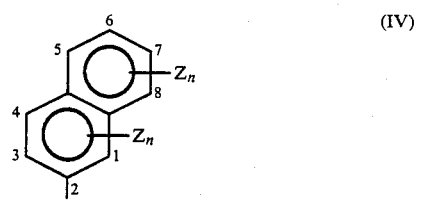

wherein Z is hydrogen, hydroxyl, amino, substituted amino, alkyl, substituted alkyl, alkenyl, aryl, substituted aryl, acyl, halogen, nitro, sulfo, carboxyl or alkoxy; n is 1, 2, or 3; provided that at least one Z in $R_1$, $R_2$ and $R_3$ is hydroxyl, amino, or substituted amino; and $Z_s$ in $Z_n$ may be the same or different, with NAD(P)H in the presence of (1) peroxidase or thiol oxide reductase and (2) diaphorase or an electron carrier, and determining the pigment thus formed.

15 Claims, No Drawings

METHOD FOR THE DETERMINATION OF THE REDUCED FORM OF NICOTINAMIDE ADENINE DINUCLEOTIDE

BACKGROUND OF THE INVENTION

The present invention relates to a method and a composition for the determination of NAD(P)H [reduced form of nicotinamide adenine dinucleotide (phosphate)].

With regard to the determination of NAD(P)H, the following methods have so far been known: (1) method for directly measuring absorption of NAD(P)H in the ultraviolet region, (2) method for deriving a fluorescent substance from NAD(P)H in the presence of diaphorase and measuring its fluorescence, and (3) method for forming formazan by reacting NAD(P)H and tetrazolium salt in the presence of diaphorase, and colorimetrically determining the formazan.

These methods have the following disadvantages. Method (1) is low in sensitivity, and is much susceptible to influences of living body components in a sample, when applied to clinical inspections, owing to the measurement in the ultraviolet region. Method (2) requires a fluorospectrophotometer. Method (3) is low in sensitivity for the determination of trace components and requires precautions for reagent preservation and measurement, because the formazan thus formed is sparingly soluble in water, with the result of deposition on the instruments, etc. The deposits are hard to remove, and most of tetrazolium salts as well as formazan are unstable to light.

Thus, development of a method for the determination of NAD(P)H with higher accuracy has been desired. As a result of studies to this end, it has been found that a pigment formed by reaction of a compound represented by the general formula (I), as will be described later, with NAD(P)H has a maximum absorption wavelength of about 600 nm and has distinguished characteristics such as less susceptibility to influences of components in a sample, particularly living body components; possible measurement in the visible region; good sensitivity; possible determination of a small amount of a sample; good solubility in water with no substantial deposition on the instruments, etc.

SUMMARY OF THE INVENTION

According to the present invention, NAD(P)H can be determined by reacting NAD(P)H with a chromogen represented by the following general formula (I) [hereinafter referred to as compound (I)]:

$$R_2-\underset{\underset{Y}{|}}{\overset{\overset{R_1}{|}}{C}}-R_3 \quad (I)$$

wherein Y is hydrogen or hydroxyl; $R_1$, $R_2$ and $R_3$ may be the same or different and are groups represented by the following general formula (II), (III) or (IV):

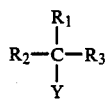   (II)

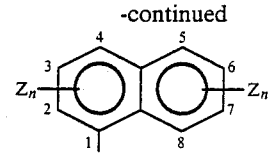   (III)

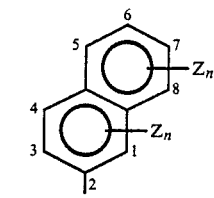   (IV)

wherein Z is hydrogen, hydroxyl, amino, substituted amino, alkyl, substituted alkyl, alkenyl, aryl, substituted aryl, acyl, halogen atom, nitro, sulfo, carboxyl or alkoxy; n is 1, 2, or 3; provided that at least one Z in $R_1$, $R_2$, and $R_3$ is hydroxyl, amino or substituted amino; and Zs in Zn may be the same or different, in the presence of (1) diaphorase or an electron carrier, and (2) peroxidase or thiol oxide reductase, and by determining the pigment thus formed.

DETAILED DESCRIPTION OF THE INVENTION

In the foregoing definitions, the alkyl includes alkyl groups having 1 to 5 carbon atoms such as methyl, ethyl, propyl, butyl, pentyl, etc., the alkenyl includes alkenyl groups having 2 to 5 carbon atoms such as vinyl, propylene, butylene, etc., and the alkoxy includes alkoxy groups having 1 to 4 carbon atoms such as methoxy, ethoxy, propoxy, butoxy, etc.

The aryl is exemplified by phenyl and naphthyl.

The acyl includes acyl groups having 2 to 5 carbon atoms, such as acetyl, propionyl, butyryl, etc., and the halogen includes a chlorine atom, a bromine atom and a fluorine atom.

The substituent in the substituted amino, substituted alkyl, and substituted aryl is exemplified by alkyl, alkenyl, aryl, alkoxy, hydroxyl, carboxyl, sulfo, sulfonyl, halogen atom, amino, alkoxycarbonylamino, alkoxycarbonyl, aminoalkyl, acyl, nitro, etc.

The alkyl, alkenyl, aryl, alkoxy, halogen, acyl, etc. in the substituent have the same meanings as defined above.

In carrying out the present invention, diaphorase or an electron carrier, for example, phenazine methosulfate (PMS), 1-methoxyphenazine methosulfate (MPMS) and Meldola's Blue, peroxidase or thiol oxide reductase, and compound (I) are generally added to a buffer solution, for example, Good's buffer, phosphate buffer, borate buffer, acetate buffer and Tris buffer to prepare a reagent solution.

The reagent solution is added to a sample, and subjected to reaction at a temperature of 30° to 50° C. at which the enzyme is not inactivated. Absorption of the reaction solution colored by the pigment thus formed is measured at the maximum absorption wavelength of the pigment in visible ray region on the basis of a reagent blank as a control, and NAD(P)H in the sample is determined from a calibration curve obtained in advance by tests on known amounts of the factor to be determined.

The present method can be applied to the determination of amount of a reactant or enzyme activity in a reaction system producing NAD(P)H by the reaction described later. When the factor to be determined is a compound, the reaction is generally carried out for about 5 to 10 minutes before the absorption measurement, and the desired factor can be determined by colorimetrically measuring the absorption of the reaction solution. When the factor is an enzyme activity, a rate of pigment formation at an appropriate time after the start of reaction is generally determined from changes in the absorbance of reaction solution, whereby the activity can be determined.

The buffer solution is used at a concentration of 10 mM to 1M. Peroxidase, thiol oxide reductase and diaphorase are used at 1 to 500 U/ml, and the electron carrier at 0.0001 to 0.01 mg/ml. Compound (I) is used at least in an equimolar amount to that of NAD(P)H which reacts with compound (I), and usually at 0.001 to 1 mg/ml.

In the reaction, the concentration of NAD(P)H in a sample is usually adjusted to 0.001 to 1 mg/ml by the reagent solution or distilled water.

When the present invention is applied to a reaction system which produces NAD(P)H, a reactant such as a substrate taking part in the reaction, an enzyme and NAD, are used generally at 0.0001 to 100 mg/ml, 10 to 1000 U/ml and 0.0001 to 100 mg/ml, respectively, though their amounts often depend on whether they are the objects to be measured or not.

A surfactant such as Triton X-100, etc. can also be used, if required, to clear the solution of turbidity.

Electron carriers have a relative activity to diaphorase, as given below, and can be used without obtaining individual calibration curves but only by using the relative activity as an index.

Procedure for determination

10 U/ml peroxidase, 0.1% Triton X-100, 0.1 mg/ml compound No. 41 and 50 mM/1 NADH are dissolved in 100 mM Good's buffer (pH 8.0) to prepare a reagent solution.

5 U/ml diaphorase, 0.001 mg/ml PMS, 0.001 mg/ml MPMS or 0.001 mg/ml of Meldola's Blue is dissolved in a predetermined amount of the reagent solution kept at 37° C. Changes in absorbance are determined at 633 nm within an exactly predetermined time. Relative activity is calculated from the changes in absorbance on the basis of diaphorase as 100.

| Electron carrier | Relative activity |
|---|---|
| Diaphorase | 100 |
| PMS | 18 |
| MPMS | 30 |
| Meldola's Blue | 20 |

Specific examples of compound (I) used in the present invention are shown in Tables 1 to 4 together with their maximum absorption wavelength ($\lambda_{max}$), sensitivity and solubility in water.

Symbols in the Tables show the following groups, and in Tables 1 to 3, the number in parenthesis shows the position, and all the positions other than those shown above indicate the presence of hydrogen.

Determination of sensitivity is carried out in the following manner:

NADH solution: NADH is added to 0.1M Tris-HCl buffer (pH 8.0) to make a solution at 0.5 mM/1.

Reagent solution: Good's buffer containing 10 U/ml peroxidase, 5 U/ml diaphorase, 0.1 mg/ml Triton X-100, and 0.1 mg/ml compound (I) (or 0.01 mg/ml nitrotetrazolium blue).

3 ml of reagent solution is added to 50 μl of NADH solution to conduct reaction. OD value is measured at $\lambda_{max}$, and the sensitivity is given as a relative value to that obtained by using nitrotetrazolium blue (NT) as 100.

Solubility is shown by A when the solubility in distilled water at 20° C. is 0.05 mg/ml or less, and by AA when it is 0.2 mg/ml or more.

M: —CH₃

E: —C₂H₅

Ph: 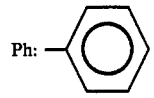

A₁: —NH— 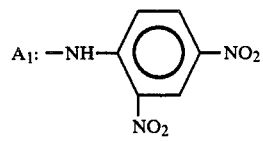 —NO₂
NO₂

A₂: —N(C₂H₅)CH₂— 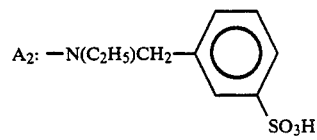
SO₃H

A₃: —N(—CH₂— 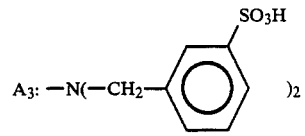 )₂
SO₃H

A₄: —NH(—CH₂— 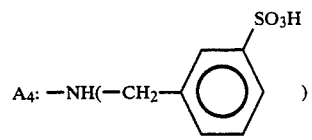 )
SO₃H

A₅: —N(C₂H₅)CH₂— 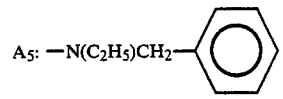

A₆: —N(CH₃)CH₂— 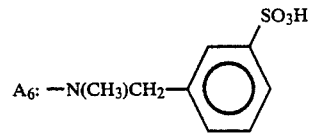
SO₃H

A₇: —N(CH₂— 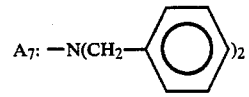 )₂

A₈: —NHC₄H₉

A₉: —NH— 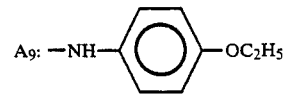 —OC₂H₅

A₁₀: —N(C₂H₅)CH₂CH₂SO₃H

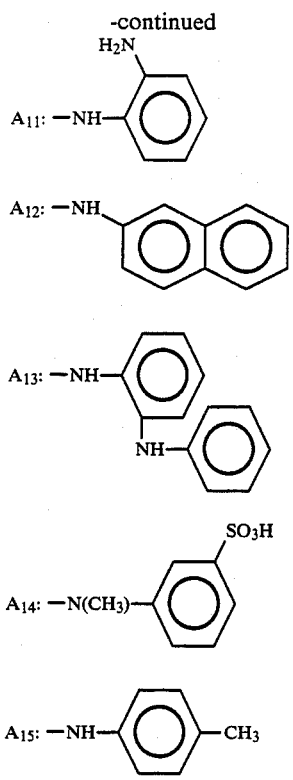

A₁₁: structure (aminophenyl-NH-)
A₁₂: structure (naphthyl-NH-)
A₁₃: structure (carbazolyl type -NH-)
A₁₄: -N(CH₃)-phenyl-SO₃H
A₁₅: -NH-phenyl-CH₃

TABLE 1

| Compound No. | Y | R₁ Formula II | R₂ Formula II | R₃ Formula II |
|---|---|---|---|---|
| 1 | H | OH(2), COOH(5) | NM₂(4) | NM₂(4) |
| 2 | OH | " | " | " |
| 3 | H | OH(2), SO₃H(5) | " | " |
| 4 | OH | " | " | " |
| 5 | H | M(2) COOH(5) | " | " |
| 6 | OH | " | " | " |
| 7 | H | A₁(3) SO₃H(4)(6) | NE₂(4) | NE₂(4) |
| 8 | OH | " | " | " |
| 9 | H | Cl(3) | NHM(4) | NHM(4) |
| 10 | OH | " | " | " |
| 11 | H | NO₂(3), M(6) | A₂(4) | A₂(4) |
| 12 | OH | " | " | " |
| 13 | H | A₃(3) | NM₂(4) | NM₂(4) |
| 14 | OH | " | " | " |
| 15 | H | A₄(3), SO₃H(6) | NE₂(4) | NE₂(4) |
| 16 | OH | " | " | " |
| 17 | H | SO₃H(4)(6) OH(3) | A₅(4) | A₅(4) |
| 18 | OH | " | " | " |
| 19 | H | SO₃H(3), OH(6) | NM₂(4) | A₃(4) |
| 20 | OH | " | " | " |
| 21 | H | Cl(3)(6) | A₆(4) | A₆(4) |
| 22 | OH | " | " | " |
| 23 | H | OH(6) | A₇(4) | A₇(4) |
| 24 | OH | " | " | " |
| 25 | H | OH(2) | A₈(4), M(3) | A₈(4), M(3) |
| 26 | OH | " | " | " |
| 27 | H | A₉(4) | A₁₀(4) | A₁₀(4) |
| 28 | OH | " | " | " |
| 29 | H | A₁₁(4) | M(2) A₂(4) | A₂(4) M(2) |
| 30 | OH | " | " | " |
| 31 | H | M(3), NH₂(4) | A₁₂(4) | A₁₂(4) |
| 32 | OH | " | " | " |
| 33 | H | A₁₃(4) | A₂(4) M(2) | A₂(4) M(2) |
| 34 | OH | " | " | " |
| 35 | H | A₁₄(4) | A₁₄(4) | A₁₄(4) |
| 36 | OH | " | " | " |

TABLE 2

| Compound No. | Y | R₁ Formula II | R₂ Formula II | R₃ Formula III |
|---|---|---|---|---|
| 37 | H | | NM₂(4) | NHPh(4) |
| 38 | OH | | " | " |
| 39 | H | NM₂(4) | NM₂(4) | OH(4), COOH(3), SO₃H(6) |
| 40 | OH | " | " | OH(4), COOH(3), SO₃H(6) |
| 41 | H | " | " | OH(2), SO₃H(3)(6) |
| 42 | OH | " | " | " |
| 43 | H | " | " | OH(2), NHE(4) |
| 44 | OH | " | " | " |
| 45 | H | " | " | A₁₅(4) |
| 46 | OH | " | " | A₁₅(4) |
| 47 | H | " | " | A₉(4) |
| 48 | OH | " | " | " |
| 49 | H | " | " | NH₂(4), SO₃H(3)(6) |
| 50 | OH | " | " | " |
| 51 | H | " | " | OH(2), SO₃H(3) |
| 52 | OH | " | " | " |
| 53 | H | " | " | OH(2), SO₃H(8) |
| 54 | OH | " | " | " |
| 55 | H | " | " | A₁₂(4) |
| 56 | OH | " | " | " |
| 57 | H | OH(4), M(3), COOH(5) | OH(4), M(3), COOH(5) | OH(2), SO₃H(3)(6) |
| 58 | OH | OH(4), M(3), COOH(5) | OH(4), M(3), COOH(5) | " |
| 59 | H | NM₂(4) | NM₂(4) | OH(2)(7) |
| 60 | OH | " | " | " |
| 61 | H | " | " | OH(2)(7) SO₃H(6) |
| 62 | OH | " | " | " |
| 63 | H | " | " | OH(2) |
| 64 | OH | " | " | " |
| 65 | H | " | " | OH(2) SO₃H(7) |
| 66 | OH | " | " | " |

TABLE 3

| Compound No. | Y | R₁ Formula II | R₂ Formula II | R₃ Formula IV |
|---|---|---|---|---|
| 67 | H | NHM(4) | NHM(4) | OH(1), SO₃H(3)(5) |
| 68 | OH | " | " | " |
| 69 | H | NM₂(4) | NM₂(4) | OH(1), SO₃H(4) |
| 70 | OH | " | " | " |
| 71 | H | " | " | OH(1), SO₃H(3)(6) |
| 72 | OH | " | " | " |
| 73 | H | " | " | OH(1)(5) |
| 74 | OH | " | " | " |
| 75 | H | " | " | OH(1), SO₃H(3) |
| 76 | OH | " | " | " |

| | | R₁: II | R₂: III | R₃: III |
|---|---|---|---|---|
| 77 | H | | OH(4), COOH(3) | OH(4), COOH(3) |
| 78 | OH | | OH(4), COOH(3) | " |

TABLE 4

| Compound No. | λmax (nm) | Sensitivity | Solubility in water |
|---|---|---|---|
| 1 | 615 | 30 | A A |
| 2 | 615 | 30 | A A |
| 3 | 623 | 120 | A A |
| 4 | 623 | 120 | A A |
| 5 | 620 | 40 | A A |
| 6 | 620 | 40 | A A |
| 7 | 630 | 80 | A A |
| 8 | 630 | 80 | A A |
| 9 | 630 | 55 | A |
| 10 | 630 | 55 | A |
| 11 | 633 | 130 | A A |
| 12 | 633 | 130 | A A |
| 13 | 627 | 180 | A |

TABLE 4-continued

| Compound No. | λmax (nm) | Sensitivity | Solubility in water |
|---|---|---|---|
| 14 | 627 | 180 | A |
| 15 | 628 | 150 | A A |
| 16 | 628 | 150 | A A |
| 17 | 615 | 45 | A A |
| 18 | 615 | 45 | A A |
| 19 | 635 | 250 | A |
| 20 | 635 | 250 | A |
| 21 | 618 | 20 | A A |
| 22 | 618 | 20 | A A |
| 23 | 633 | 450 | A A |
| 24 | 633 | 450 | A A |
| 25 | 645 | 300 | A A |
| 26 | 645 | 300 | A A |
| 27 | 598 | 50 | A A |
| 28 | 598 | 50 | A A |
| 29 | 618 | 85 | A A |
| 30 | 618 | 85 | A A |
| 31 | 631 | 45 | A A |
| 32 | 631 | 45 | A A |
| 33 | 653 | 40 | A A |
| 34 | 653 | 40 | A A |
| 35 | 647 | 55 | A A |
| 36 | 647 | 55 | A A |
| 37 | 617 | 50 | A |
| 38 | 617 | 50 | A |
| 39 | 598 | 35 | A A |
| 40 | 598 | 35 | A A |
| 41 | 633 | 800 | A A |
| 42 | 633 | 800 | A A |
| 43 | 640 | 500 | A |
| 44 | 640 | 500 | A |
| 45 | 595 | 200 | A A |
| 46 | 595 | 200 | A A |
| 47 | 644 | 350 | A A |
| 48 | 644 | 350 | A A |
| 49 | 590 | 80 | A A |
| 50 | 590 | 80 | A A |
| 51 | 634 | 140 | A A |
| 52 | 634 | 140 | A A |
| 53 | 630 | 150 | A A |
| 54 | 630 | 150 | A A |
| 55 | 615 | 60 | A A |
| 56 | 615 | 60 | A A |
| 57 | 605 | 110 | A A |
| 58 | 605 | 110 | A A |
| 59 | 635 | 700 | A A |
| 60 | 635 | 700 | A A |
| 61 | 633 | 750 | A A |
| 62 | 633 | 750 | A A |
| 63 | 634 | 200 | A A |
| 64 | 634 | 200 | A A |
| 65 | 633 | 50 | A A |
| 66 | 633 | 50 | A A |
| 67 | 643 | 280 | A A |
| 68 | 643 | 280 | A A |
| 69 | 633 | 120 | A A |
| 70 | 633 | 120 | A A |
| 71 | 625 | 270 | A A |
| 72 | 625 | 270 | A A |
| 73 | 633 | 280 | A A |
| 74 | 633 | 280 | A A |
| 75 | 635 | 220 | A A |
| 76 | 635 | 220 | A A |
| 77 | 628 | 75 | A A |
| 78 | 628 | 75 | A A |
| NT | 530 | 100 | B |

NT: nitrotetrazolium blue

Compound (I) is a compound known as an intermediate for dye synthesis, and the compounds listed in Tables 1 to 3 can be prepared in the following manner:

Process 1

4,4'-bis(dimethylamino)benzhydrol is reacted with an equimolar amount of substituted benzene or substituted naphthalene given below in 2 to 10-fold amount of 60% sulfuric acid on the basis of the total starting compounds. The reaction is carried out at 50° to 100° C. with stirring for 2 to 3 hours. Then, 5 to 6-fold amount of cold water of about 5° C. is added to the reaction solution, and the mixture is stirred overnight.

The reaction product is recovered therefrom by filtration washed with 8% sulfuric acid, and dried in vacuo, whereby the desired compound the group Y of which is hydrogen is obtained.

The compound is hydrolized with alkali to obtain the desired compound, the group Y of which is hydroxyl.

$A_1$: benzene ring with $X_1$, $X_2$ substituents $A_2$: naphthalene ring with positions 1, 2, 3, 4, 5, 6, 7, 8

| Compound No. | A | $X_1$ | $X_2$ |
|---|---|---|---|
| 1, 2 | $A_1$ | OH | COOH |
| 3, 4 | " | " | $SO_3H$ |
| 5, 6 | " | $CH_3$ | COOH |

| Compound No. | groups in starting material ($A_2$) |
|---|---|
| 39, 40 | OH(2), COOH(3), $SO_3H$(8) |
| 41, 42 | $SO_3H$(3), OH(4) |
| 43, 44 | NH($C_2H_5$)(2), OH(4) |
| 49, 50 | $NH_2$(2), $SO_3H$(3)(8) |
| 51, 52 | $SO_3H$(3), OH(4) |
| 53, 54 | OH(4), $SO_3H$(6) |
| 59, 60 | OH(4)(7) |
| 61, 62 | OH(4)(7) |
| 63, 64 | OH(4)(7) |
| 65, 66 | OH(4), $SO_3H$(7) |
| 69, 70 | $SO_3H$(2), OH(5) |
| 71, 72 | $SO_3H$(2), OH(5) $SO_3H$(8) |
| 73, 74 | OH(1)(5) |
| 75, 76 | $SO_3H$(3), OH(5) |

All the positions other than those shown above indicate the presence of hydrogen.

Process 2

Well known pigments corresponding to the individual compounds in the following Table are used as starting compounds and dissolved in 80-fold amount of distilled water on the basis of the weight of the starting compounds. 2-fold amount of sodium boron hydride on the basis of the weight of the starting pigment is slowly added to the individual pigment solutions to conduct reduction reaction. After stirring at room temperature for about 2 hours, the reaction solutions are concentrated to dryness in a rotary evaporator. Then, dried residues are dissolved in a minimum necessary amount of distilled water for dissolving the dried residues. The solution is charged on the column packed with 15 to 20-fold volume of resin HP-20 on the basis of the solution. Then, 3 to 4-fold volume of distilled water on the basis of the resin used is passed therethrough to remove the remaining sodium boron hydride. At that time, the desired products remain as adsorbed on HP-20. Then, a developing solvent of methanol:distilled water=1:1 is passed therethrough to recover the eluate in appropriate fractions. After the desired compound in the eluate is ascertained by UV monitor or by TLC, the fractions containing the compound are joined together, and concentrated to dryness, to obtain the desired compound, the group Y of which is hydrogen. The compound is hydrolized with alkali to obtain the desired compound, the group Y of which is hydroxyl.

| Compound No. | Color index No. | Compound No. | Color index No. | Compound No. | Color index No. |
|---|---|---|---|---|---|
| 7, 8 | 42050 | 77, 78 | 44530 | 35, 36 | 42790 |
| 13, 14 | 42038 | 29, 30 | 42635 | 15, 16 | 42046 |
| 55, 56 | 44095 | 31, 32 | 42700 | 17, 18 | 42052 |
| 57, 58 | 44100 | 33, 34 | 42715 | 37, 38 | 44000 |
| 45, 46 | 44085 | 47, 48 | 44065 | 27, 28 | 42675 |

Process 3

Preparation of compounds Nos. 9, 10, 67 and 68:

At first, 4,4'-bis(dimethylamino)benzhydrol and chlorobenzene (compounds Nos. 9 and 10) or 1-naphthol-3,5-disulfonic acid (compounds Nos. 67 and 68) are subjected to condensation in the same manner as in Process 1 above, using 60% sulfuric acid. The compounds thus obtained are dissolved in an appropriate amount of acetic acid, and one of the two methyl groups is released from the dimethylamino group using lead oxide as a catalyst, whereby compound No. 9 or 67 is obtained. Compound No. 10 or 68 is obtained by hydrolysis of compound No. 9 or 67 with alkali.

Process 4

Preparation of compounds Nos. 11 and 12:

At first, 2-methyl-5-nitrobenzaldehyde and α-(N-methylanilino)-m-toluenesulfonic acid are added in a molar ratio of 1:2 to 10-fold amount of sulfuric acid on the basis of the weight of total starting compounds and the mixture is stirred at about 100° C. for 120 hours. The precipitates are immediately filtered through a glass filter, washed with 5% sulfuric acid, and dried in vacuo, whereby compound No. 11 is obtained. Compound No. 12 is obtained by hydrolysis of compound No. 11 with alkali.

Process 5

Preparation of compounds Nos. 19 and 20:

At first, 2-hydroxybenzaldehyde, N,N-dimethylaniline and N-phenylbenzylamine are added in a molar ratio of 1:1:1 to 10-fold amount of 80% sulfuric acid on the basis of the weight of total starting compounds, and the mixture is stirred at about 190° C. for 120 hours. The precipitates are immediately filtered through a glass filter, washed with 5% sulfuric acid, and dried in vacuo to obtain compound No. 19. Compound No. 20 is obtained by hydrolysis of compound No. 19 with alkali.

Process 6

Preparation of compounds Nos. 21 and 22:

At first, 2,5-dichlorobenzaldehyde and α-(N-methylanilino)-m-toluenesulfonic acid are added in a molar ratio of 1:2 to 10-fold amount of sulfuric acid on the basis of the weight of total starting compounds, and the mixture is stirred at about 100° C. for 120 hours. The precipitates are immediately filtered through a glass filter, washed with 5% sulfuric acid and dried in vacuo to obtain compound No. 21. Compound No. 22 is obtained by hydrolysis of compound No. 21 with alkali.

Process 7

Preparation of compounds Nos. 23, 24, 25 and 26:

At first, 2-hydroxybenzaldehyde and N-phenyldibenzylamine (Nos. 23 and 24), or N-butyl-o-toluidine (Nos. 25 and 26) are added in a molar ratio of 1:2 to 10-fold amount of sulfuric acid on the basis of the weight of starting compounds, and the mixture is stirred at about 100° C. for 120 hours. The precipitates are immediately filtered through a glass filter, washed with 5% sulfuric acid, and dried in vacuo to obtain compound No. 23 or 25. Compound No. 24 or 26 is obtained by hydrolysis of compound No. 23 or 25 with alkali.

Compounds other than those described above can be prepared by selecting the starting compounds according to the desired compounds by said procedures or in the manner as disclosed in the known literature, for example, Color Index, Volume 4.

The present method can be applied to the determination of amount of a reactant or enzyme activity in a reaction system which can stoichiometrically produce NAD(P)H by reaction. Many reaction systems using NAD and dehydrogenase are known as such reaction system. The factors to be determined include, for example, glucose, galactose, lactic acid, alcohol, malic acid, aldehydes, xanthine, cholesterol, bile acid, lactate dehydrogenase (LDH) activity and neutral fat.

These reaction systems are shown schematically.

1. Glucose

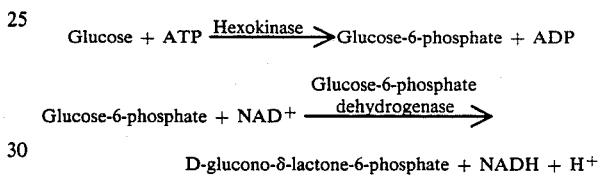

D-glucono-δ-lactone-6-phosphate + NADH + H$^+$

2. Galactose

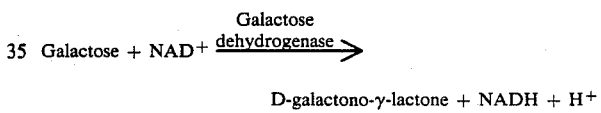

D-galactono-γ-lactone + NADH + H$^+$

3. Lactic acid

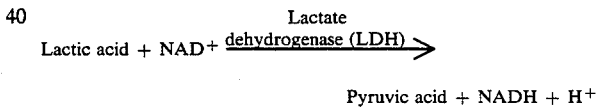

Pyruvic acid + NADH + H$^+$

4. Alcohol

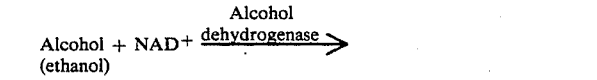

Aldehyde + NADH + H$^+$
(acetaldehyde)

5. Malic acid

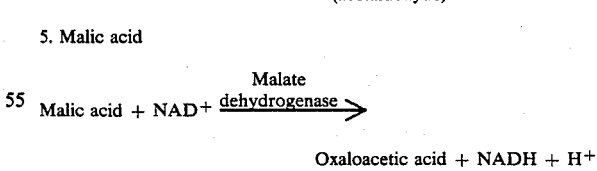

Oxaloacetic acid + NADH + H$^+$

6. Aldehyde

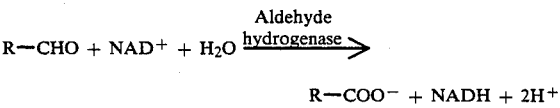

R—COO$^-$ + NADH + 2H$^+$

7. Xanthine

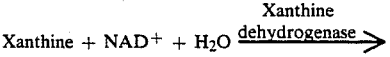

Uric acid + NADH + H⁺

8. Neutral fat and glycerol

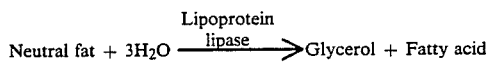

Neutral fat + 3H₂O $\xrightarrow{\text{Lipoprotein lipase}}$ Glycerol + Fatty acid

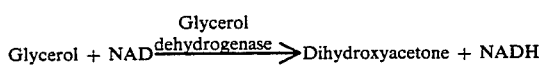

Glycerol + NAD $\xrightarrow{\text{Glycerol dehydrogenase}}$ Dihydroxyacetone + NADH

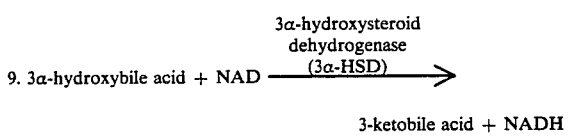

9. 3α-hydroxybile acid + NAD $\xrightarrow{\text{3α-hydroxysteroid dehydrogenase (3α-HSD)}}$ 3-ketobile acid + NADH A composition for the determination of NAD(P)H in the present invention comprises (a) peroxidase or thiol oxide reductase, (b) diaphorase or an electron carrier, and (c) compound (I). A buffer can be added to the composition, if required.

A composition containing a necessary substrate or enzyme, in view of the factor to be determined or kits separately prepared for later combination will be very convenient and useful for determination of various substances or enzyme activities.

Certain specific embodiments of the present invention are illustrated in the following representative examples.

EXAMPLE 1

Determination of total bile acids:

| Reagent solution | |
| --- | --- |
| Peroxidase | 1000 U |
| Diaphorase | 500 U |
| 3α-HSD | 50 U |
| NAD | 660 mg |
| Trition X-100 | 100 mg |
| Chromogen | |
| compound No. 41 | 10 mg (1) |
| compound No. 59 | 10 mg (2) or |
| compound No. 61 | 10 mg (3) |

These materials are dissolved in 100 ml of 100 mM Good's buffer (pH 6.5).

100 μl of serum and 3 ml of the reagent solution are placed into a test tube and the test tube is left standing at 37° C. for 10 minutes. Then, absorbance of the reaction solution at λ$_{max}$ of the chromogen is measured in contrast to a reagent blank test as a control, and total bile acid concentration of the serum is calculated by a calibration curve prepared in advance.

Another reagent solution prepared by adding 3α-HSD, NAD, diaphorase, Triton X-100 and 15 mg of nitrotetrazolium blue (NT) to the said buffer in the same manner as above is also used.

Results are shown in Table 5 in comparison with measurements by gas chromatography (GC).

TABLE 5

| | Total bile acid content (μM/l) | | | | |
| --- | --- | --- | --- | --- | --- |
| Serum No. | GC | NT | (1) | (2) | (3) |
| 1 | 9.5 | 15.2 | 10.0 | 9.8 | 9.5 |
| 2 | 5.3 | 11.3 | 5.1 | 5.4 | 5.1 |
| 3 | 12.8 | 23.1 | 13.1 | 12.6 | 13.0 |
| 4 | 6.4 | 8.8 | 5.8 | 6.0 | 6.1 |

TABLE 5-continued

| | Total bile acid content (μM/l) | | | | |
| --- | --- | --- | --- | --- | --- |
| Serum No. | GC | NT | (1) | (2) | (3) |
| 5 | 7.1 | 4.2 | 7.5 | 6.9 | 7.1 |

EXAMPLE 2

Determination of LDH activity:

| Reagent solution | |
| --- | --- |
| Peroxidase | 1000 U |
| MPMS | 1.5 mg |
| Sodium L-lactate | 50 mg |
| NAD | 100 mg |
| Triton X-100 | 100 mg |
| Chromogen | |
| compound No. 53 | 10 mg (1) |
| compound No. 69 | 10 mg (2) or |
| compound No. 75 | 10 mg (3) |

These materials are dissolved in 100 ml of 100 mM Good's buffer (pH 8.2).

After the reagent solution is heated at 37° C. for 10 minutes, 20 μl of serum is added thereto, and exactly 1 minute and 3 minutes thereafter, absorbance of the reaction solution is measured at λ$_{max}$ of the chromogen in contrast with a reagent black test. A difference between the absorbance 3 minutes thereafter and that 1 minute thereafter is calculated, and LDH activity in serum is calculated by a calibration curve prepared in advance.

Another reagent solution prepared by dissolving MPMS, sodium L-lactate, Triton X-100, NAD and 10 mg of nitrotetrazolium blue (NT) in said buffer in the same manner as above is also used.

Results are shown in Table 6 in comparison with the measurements according to the UV method.

TABLE 6

| | LHD activity (IU/l) | | | | |
| --- | --- | --- | --- | --- | --- |
| Serum No. | UV | NT | (1) | (2) | (3) |
| 1 | 120 | 138 | 125 | 117 | 122 |
| 2 | 85 | 115 | 90 | 85 | 88 |
| 3 | 432 | 620 | 415 | 450 | 423 |
| 4 | 62 | 58 | 60 | 62 | 60 |
| 5 | 218 | 290 | 220 | 209 | 225 |

EXAMPLE 3

Determination of neutral fat:

| Reagent solution | |
| --- | --- |
| Peroxidase | 1000 U |
| Diaphorase | 500 U |
| Lipoprotein lipase | 5000 U |
| Glycerol dehydrogenase | 5000 U |
| NAD | 500 mg |
| Triton X-100 | 100 mg |
| Chromogen | |
| compound No. 71 | 10 mg (1) |
| compound No. 63 | 10 mg (2) or |
| compound No. 65 | 10 mg (3) |

These materials are dissolved in 100 ml of 100 mM Good's buffer (pH 6.75).

20 μl of serum and 3 ml of the reagent solution are placed in a test tube and the test tube is left standing at 37° C. for 10 minutes. Then, absorbance of the reaction solution is measured at λ$_{max}$ of the chromogen in contrast with a reagent blank test, and concentration of neutral fat in the serum is calculated by a calibration curve prepared in advance.

Another reagent solution prepared by adding diaphorase, lipoprotein lipase, glycerol dehydrogenase, NAD, Triton X-100, and 15 mg of nitrotetrazolium blue to said buffer in the same manner as above is also used.

Results are shown in Table 7 in comparison with measurements in a system (A) using glycerol oxidase and peroxidase.

TABLE 7

| Serum No. | Neutral fat content (mg/dl) | | | | |
|---|---|---|---|---|---|
| | A | NT | (1) | (2) | (3) |
| 1 | 83 | 92 | 83 | 81 | 83 |
| 2 | 110 | 131 | 108 | 112 | 109 |
| 3 | 163 | 182 | 158 | 160 | 163 |
| 4 | 62 | 50 | 60 | 61 | 60 |
| 5 | 74 | 85 | 74 | 77 | 75 |

What is claimed is:

1. A method for the determination of NAD(P)H comprising the steps of: reacting a chromogen represented by formula (I):

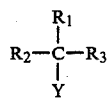

wherein Y is hydrogen or hydroxyl; $R_1$, $R_2$ and $R_3$ are independently selected from the group consisting of (II), (III) and (IV):

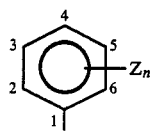

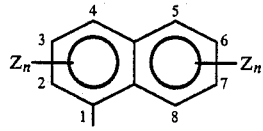

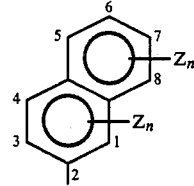

wherein Z is independently selected from the group consisting of hydrogen, hydroxyl, optionally substituted amino, optionally substituted alkyl, alkenyl, optionally substituted aryl, acyl, halogen, nitro, suflo, carboxyl and alkoxy, wheren n is 1, 2 or 3 and the optional substituent is selected from the group consisting of alkyl, alkenyl, aryl, alkoxy, hydroxyl, carboxyl, sulfo, sulfonyl, halogen, amino, alkoxycarbonylamino, alkoxycarbonyl, aminoalkyl, acyl and nitro; provided that at least one Z in $R_1$, $R_2$ and $R_3$ is hydroxyl or optionally substituted amino; with NAD(P)H in the presence of (1) peroxidase or thiol oxide reductase and (2) diaphorase or an electron carrier; determining the pigment thus formed, said pigment being determined in the absence of $Mn^{2+}$ or $Co^{2+}$ ion; and determining NAD(P)H from a calibration curve.

2. A method according to claim 1, wherein $R_1$ and $R_2$ are formula (II).

3. A method according to claim 2, wherein $R_3$ is also formula (II).

4. A method according to claim 1, wherein said electron carrier is selected from the group consisting of PMS, MPMS and Meldola's Blue.

5. A method according to claim 1, wherein said NAD(P)H is provided by a reaction system which produces NAD(P)H.

6. A method according to claim 5, wherein said reaction system comprises the reaction of NAD with a second reactant in the presence of an enzyme.

7. A method according to claim 6, wherein said second reactant is selected from the group consisting of glucose-6-phosphate, galactose, lactic acid, alcohol, malic acid aldehyde, xanthine, glycerol and 3α-hydroxybile acid.

8. A method according to claim 1, wherein said determination of pigment is carried out by photometric measurement.

9. A method according to claim 8, wherein said measurement is carried out by measuring the absorption of the reaction solution.

10. A method according to claim 9, wherein said absorption is measured using rays having wavelengths in the visible ray region.

11. A method according to claim 8, wherein said measurement is carried out by measuring the rate of absorption change of reaction solution.

12. A method according to claim 1, wherein said reaction is carried out in a buffer.

13. A method according to claim 1, using peroxidase and diaphorase.

14. A composition for the determination of NAD(P)H, comprising (a) peroxidase or thiol oxide reductase, (b) diaphorase or an electron carrier, and (c) a compound represented by formula (I) of claim 1, said composition being further characterized as containing no $Mn^{2+}$ or $Co^{2+}$ ion.

15. A composition according to claim 13, wherein said composition further comprises NAD and an enzyme which catalyzes a reaction of NAD with a substrate.

* * * * *

UNITED STATES PATENT AND TRADEMARK OFFICE
CERTIFICATE OF CORRECTION

PATENT NO. : 4,824,779
DATED : April 25, 1989
INVENTOR(S) : NORIHITO AOYAMA, ET AL.

It is certified that error appears in the above-identified patent and that said Letters Patent is hereby corrected as shown below:

COLUMN 13

Line 58, "suflo," should read --sulfo,--.

Signed and Sealed this

Twenty-sixth Day of November, 1991

Attest:

HARRY F. MANBECK, JR.

*Attesting Officer*    *Commissioner of Patents and Trademarks*